(12) United States Patent
Davis et al.

(10) Patent No.: US 10,551,351 B1
(45) Date of Patent: Feb. 4, 2020

(54) SYSTEM AND METHOD FOR EFFICIENTLY REVIEWING WELD SCAN DATA BY A WELD INSPECTOR

(71) Applicant: VeriPhase, Inc., Birmingham, AL (US)

(72) Inventors: John Mark Davis, Hoover, AL (US); Archibald Leach Cobbs, Mountain Brook, AL (US); Samuel Matthew Davis, Birmngham, AL (US); Charles Allan Hansen, Sterrett, AL (US)

(73) Assignee: VeriPhase, Inc., Birmingham, AL (US)

( * ) Notice: Subject to any disclaimer, the term of this patent is extended or adjusted under 35 U.S.C. 154(b) by 276 days.

(21) Appl. No.: 15/866,571

(22) Filed: Jan. 10, 2018

Related U.S. Application Data

(62) Division of application No. 14/986,195, filed on Dec. 31, 2015, now Pat. No. 10,324,066.

(51) Int. Cl.
*G01N 29/04* (2006.01)

(52) U.S. Cl.
CPC ... *G01N 29/043* (2013.01); *G01N 2291/0234* (2013.01); *G01N 2291/044* (2013.01)

(58) Field of Classification Search
CPC .............. G01N 29/44; G01N 29/4445; G01N 2291/044; G01N 2291/0234; G01N 2291/0289; G01N 2291/267–2677
See application file for complete search history.

(56) References Cited

U.S. PATENT DOCUMENTS

| | | | |
|---|---|---|---|
| 4,967,381 A * | 10/1990 | Lane | G05B 15/02 700/17 |
| 5,907,100 A * | 5/1999 | Cook | G01N 29/2412 73/602 |
| 6,175,380 B1 * | 1/2001 | Van Den Bosch | E21B 47/0002 348/125 |
| 6,813,949 B2 * | 11/2004 | Masaniello | F17D 5/02 73/602 |
| 10,324,066 B1 * | 6/2019 | Davis | G01N 29/043 |
| 2007/0032968 A1 * | 2/2007 | Nakamura | G01H 1/003 702/56 |
| 2007/0157730 A1 * | 7/2007 | Ochiai | F22B 37/003 73/627 |

(Continued)

*Primary Examiner* — Natalie Huls
(74) *Attorney, Agent, or Firm* — The Gache Law Firm, P.C.; Russell C. Gache

(57) ABSTRACT

A system is disclosed that increases the efficiency of a weld inspector by reducing the amount of weld data that needs to be examined for any non-destructive ("NDT") phased array and time-of-flight, diffraction ultrasonic testing of welds. The system reads ultrasonic testing data from an NDT scan of a series of metal welds and creates a table of target weld indications ranked by a series of filters representative of predetermined exclusion and significance criteria. The invention acts as a weld analysis concentrator by focusing the attention of an inspector on potential weld flaws that merit their attention, thereby increasing the efficiency of the inspector. The process typically reduces 95% to 98% of the ultrasonic weld testing data that must be reviewed by the inspector, while retaining flaw indications necessary for an inspector's competent review in conformity with various code requirements and regulations.

20 Claims, 9 Drawing Sheets
(1 of 9 Drawing Sheet(s) Filed in Color)

(56) References Cited

U.S. PATENT DOCUMENTS

| | | |
|---|---|---|
| 2014/0238136 A1* | 8/2014 | Ten Grotenhuis ........................... G01N 29/0654 73/592 |
| 2016/0231278 A1* | 8/2016 | Goroshevskiy ........ G01N 27/82 |
| 2017/0169128 A1* | 6/2017 | Batchu Krishnaiahsetty .............. H04N 1/32122 |
| 2018/0031152 A1* | 2/2018 | Rajagopalan ........ B23K 37/003 |
| 2019/0026935 A1* | 1/2019 | Podziemski ............ G06T 15/08 |

\* cited by examiner

FIG. 8

SYSTEM AND METHOD FOR EFFICIENTLY REVIEWING WELD SCAN DATA BY A WELD INSPECTOR

FIELD OF THE INVENTION

The present invention relates generally to software tools for accelerating and enhancing the data analysis of non-destructive testing using ultrasonic sound waves in base metal and welded materials. In particular, the present invention relates to improving efficient analysis of ultrasonic weld data pertaining to pipe, plate, and structural weld seams. In even greater particularity, the present invention relates to assisted data analysis of ultrasonic phased array testing data to increase the speed, reliability, evaluation, and reporting efficiency for code compliance of weld inspectors.

BACKGROUND OF THE INVENTION

Bridges, buildings, railroads, pipes, vessels, tanks, and other metal or steel welded structures are a vital part of modern infrastructure. These structures are typically fabricated from sets of discrete metal sub-components that are welded together to form a critical component and/or a total system. Welded seams and other weld joining points must be fused into a welded unit having satisfactory strength to ensure building code compliance and to achieve proper structural integrity of the entire system, and/or to ensure meeting the purpose of the design for which it was intended. For example, a pressure vessel or fluid tank must have water tight exterior as well as provide structural support for the entire vessel or tank system. Pipes and vessels similarly must have water or gas sealed, welded seams to ensure the integrity of the pipe/vessel and to properly isolate the fluid or gas held by the pipe from the environment. In addition, these systems deteriorate over time due to operational and environmental factors such as, residual and applied stresses, vibration, rain, snow, strong winds, temperature variance, earthquakes, oxidation, material fatigue, and other changes that occur over the passage of time. Hence, nondestructive testing of welds and metal structures, and their components, are utilized after initial fabrication, installation, and periodically thereafter, to ensure a structure's integrity. Further, both for new construction and routine periodic maintenance, careful analysis of the weld joints in each structure is necessary to ensure satisfaction of various weld specifications, industry codes, and construction regulations. For example, the American Society Mechanical Engineers ("ASME"), the American Welding Society ("AWS"), and the American Petroleum Institute ("API"), among others, each have their own welding codes, procedures, and specifications.

Modern inspectors use non-destructive test ("NDT") equipment to inspect constructed metal (e.g. steel) structures and their weld joints. These inspection devices use ultrasonic wave generators to take digital "snap-shots" of welds from which an inspector may verify weld integrity and to ensure compliance with welding codes and specifications. Ultrasonic technology is used to detect internal and surface breaking flaws in the weld and the base metal, which are not visible externally, and is based on the principle that a gap or defect in the weld changes the propagation of ultrasonic sound through the metal. One common method of NDT testing uses conventional, single-probe ultrasonic testing requiring an operator's interpretation of a screen similar to an oscilloscope screen that presents time and amplitude information. Another method uses an array of ultrasonic phased array sensors to test a structure. Such methods can be combined into a single digital piece of inspection equipment that uses phased array ("PA") and time-of-flight ("TOFD") diffraction methodologies to provide a three dimensional image of a weld displayed on a color screen. An inspector then evaluates the potential for a flaw or defect in the weld by reviewing the screen. Such ultrasonic testing ("UT") equipment is typically highly mobile, and allows for the recordation of ultrasonic data for the analysis of welded areas in joined metal pieces. For example, Olympus NDT, Inc. markets and sells ultrasonic units through its OmniScan™ and Epoch™ lines of weld flaw detectors. The Olympus ultrasonic inspection systems include conventional ultrasonic flaw detectors, which use ultrasonic waveforms to detect flaws, and advanced ultrasonic phased array flaw detectors, which create internal cross-section images of the areas being inspected. These ultrasonic flaw detectors may also be configured to do a phased array ultrasonic testing ("PAUT") inspection that produces encoded digital data points on welds which may be further processed at a later time. The data may also be reviewed later at a time convenient for an inspector and in an environment away from the component or structure's location, which is typically more suitable for detailed analysis work. Such ultrasonic data is recorded and saved in large data files which may be retrieved for evaluation by an inspector using specialized software applications. While these data files are readable by the ultrasonic testing device, software applications also exist that assist in the evaluation and visual display of such inspection data on common computing devices, such as a PC. An example of such applications is the OmniPC™ analysis software also available from Olympus NDT, Inc., along with an additional analysis tool set called TomoView™. Both of these tools allow for a more precise and reliable review of the three dimensional PA data by an inspector.

A phased array data file consists of captured data representative of continuous A-scans along a weld which may be processed to create a three dimensional data set representative of the top, side, and end views of a weld joint. Within each A-scan, a series of recorded data points record an intensity or amplitude value from 0% to 100% of ultrasonic signal reflections. These data points are then saved as OPD, RTD or TV file formats for subsequent analysis. Since the recordation of ultrasonic data is correlated to the exact PA probe position on the structure being tested, the inspector may use the analysis software including various sets of sophisticated analysis tools to review the recorded data in a number of geometric views and orientations (e.g. top view, side view, end view) to improve inspection review accuracy.

Further information regarding the use of phased array UT equipment, configuring such UT equipment, establishing a test scan plan applicable to a particular inspection or weld joint design situation, the recording of that data in various file formats, the physics and geometries of the ultrasonic sound beams and resulting scanning views in UT, the use and applicability of "data" libraries, the storing of testing data files, the usage of different types of scan views, the visual analysis of weld flaw indications, and the generation of inspection reports based upon UT shall not be discussed herein as such information is well known known in the NDT industry and not necessary for a complete understanding of the disclosed invention. However, Applicant references and hereby incorporates by reference the treatise *UT Classroom Training Book*, Paul T. Marks, ISDN No. 978-1-57117-345-4 (e-book), published by The American Society for Nondestructive Testing, and two treatises published by Olympus NTD, Inc: (1) *Introduction to Phased Array Ultrasonic Technology Applications*, third printing 2007, ISBN No. 0-9735933-4-2; and (2) *Advances in Phased Array Ultrasonic Technology Applications*, 2007, ISBN No. 0-9735933-4-2. The books may be obtained at the ASNT website www.asnt.org or the Olympus NDT resources website www.olympus-ims.com. These treatises explain the above subjects in detail and the general theory of UT using modern equipment. Further, Applicant references and hereby incorporates by reference U.S. Pat. Nos. 8,156, 813B2, 8,577,629B2, 9,032,802B2, 9,081,490B2. These patents discuss and disclose background information regarding the electronics and theory behind PA ultrasonic testing.

Nevertheless, even with modern PA and time-of-flight UT devices, and even when inspection analysis is conducted in an environment conducive for careful study, the data analysis and reporting process can be a tedious and fatiguing task for inspectors. For example, metal pipe and plate structures typically have girth welds and long seams that must be inspected. PA ultrasonic and time-of-flight, diffraction inspection for those welds seams can produce extremely large data files requiring many hours of data review and analysis of all data points along the weld seams by an inspector. Usually most of the data points are nominal, satisfactory welds, creating a monotonous review period and potentially reducing weld flaw recognition by an inspector due to fatigue. Hence, what would enhance the inspection process would be a system for focusing an inspector's attention on actual weld defect indications, by excluding data points that present satisfactory and acceptable weld characteristics. Such a system would improve an inspector's efficiency and accuracy in conducting new or reviewing prior weld inspections, thereby saving time and money.

SUMMARY OF THE INVENTION

In summary, the invention reads data from PAUT or TOFD data files that capture ultrasonic testing results from a series of metal welds, or a set of continuous welded metal seams, and creates a table of target indications requiring an inspector's review and evaluation. The invention reads one or more testing data files and collects weld indications from the data files, applies a series of filters to each recorded indication, and ranks the indications in a meritorious order, including the application of color coding to these indications to assist the inspector in analysis of the testing data file. The invention acts as a weld analysis concentrator by focusing the attention of an inspector on weld targets that merit their attention, thereby increasing the efficiency of the inspector. The process typically excludes 95% to 98% of the weld data, while retaining significant flaw indications necessary for an inspector's review and in conformity with inspection regulations from various organizations establishing weld codes and specifications.

Other features and objects and advantages of the present invention will become apparent from a reading of the following description as well as a study of the appended drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A system incorporating the features of the invention is depicted in the attached drawings which form a portion of the disclosure and wherein.

DESCRIPTION OF THE PREFERRED EMBODIMENTS

Figure 1:
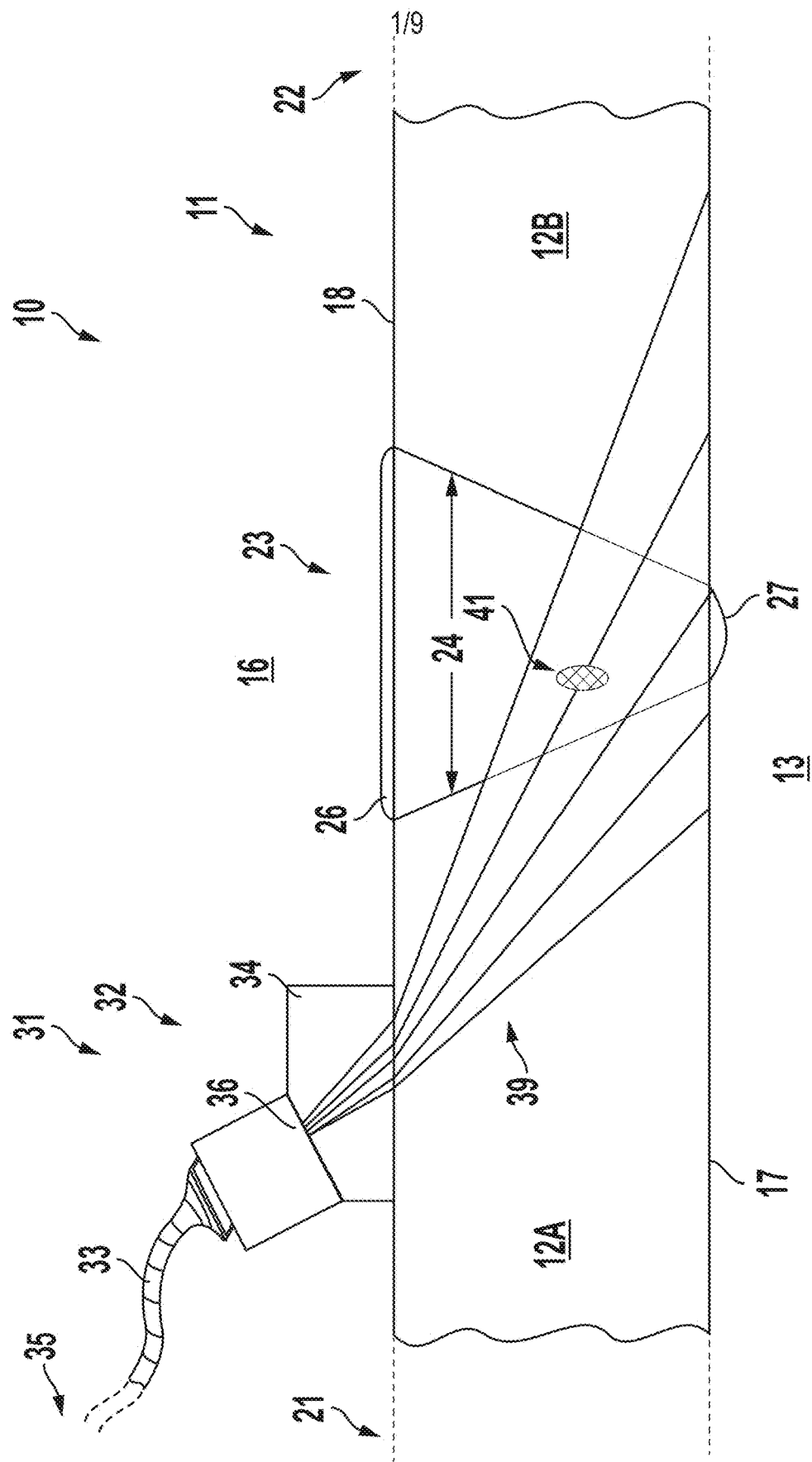
FIG. 1 a side view of a typical ultrasonic testing system for a pipe weld seam using a phased array or time-of-flight inspection system.

Referring to the drawings for a better understanding of the function and structure of the invention, FIG. 1 shows a side view 10 of a typical ultrasonic testing scenario for a steel pipe weld seam using a phased array ultrasonic tester. The pipe 11 includes two sections 12a and 12b joined together via weld seam 23. Each piece of the pipe separates the environment in which it is positioned into an interior 13 and an exterior 16, with each pipe section having an interior surface 17 and exterior surface 18 contacting the interior and exterior spaces. As may be noted, this arrangement would be similar for other weld joint designs such as vessels, tanks, and structural members. Each section 12a and 12b extends away from weld seam 23 curving downwards on each side 21, 22 to enclose interior 13. The weld seam 23 is typically "V" shaped having an upper width 24 larger than bottom width 27, but may have other shapes as is known. The top of weld 23 typically has a portion of excess weld material 26 that extends slightly above the exterior of the pipe 18 for reinforcement.

Positioned adjacent to the pipe 11 is a phased array UT probe 31 including a transducer probe 32 having an angled probe wedge 34, an ultrasonic array transmitter and receiver element 36, and a connection cord 33 connected to a testing device 35 (not shown). In addition to an electrical signal wire, such as a coaxial cable, the cord 33 may also include a tube for the transmission of water or other fluid (known as "couplant") in which to couple the phased array probe and wedge to the base material and in order to efficiently transmit the ultrasonic sound waves into the base metal and weld metal.

The probe 36 emits ultrasonic waves from elements held in probe 31 that are controlled by testing device 35 at timed intervals to create various types of wave fronts or sound beams that are propagated through the metal of the base metal 11 and the weld material 23. This results in a series of longitudinal wave beams or shear wave beams 39. The sonic beams 39 vary in angle generally from about 45 degrees to 70 degrees, refracting through the weld 23 and surrounding base metal 12a,12b, and produce ultrasonic reflections received by probe 31 that are sent back to testing device 35. The combination of the wave segments 39, software that controls the timing, frequency, emission position, and other qualities of those sound wave beams, and the position of the probe 31 adjacent to the weld seam 23, is designed to reveal weld flaws 41 that may be present in or around the weld seam. The wave beams 39 will typically generate reflections off the interior surface 17 and exterior surface 18 (not shown).

Figure 2:
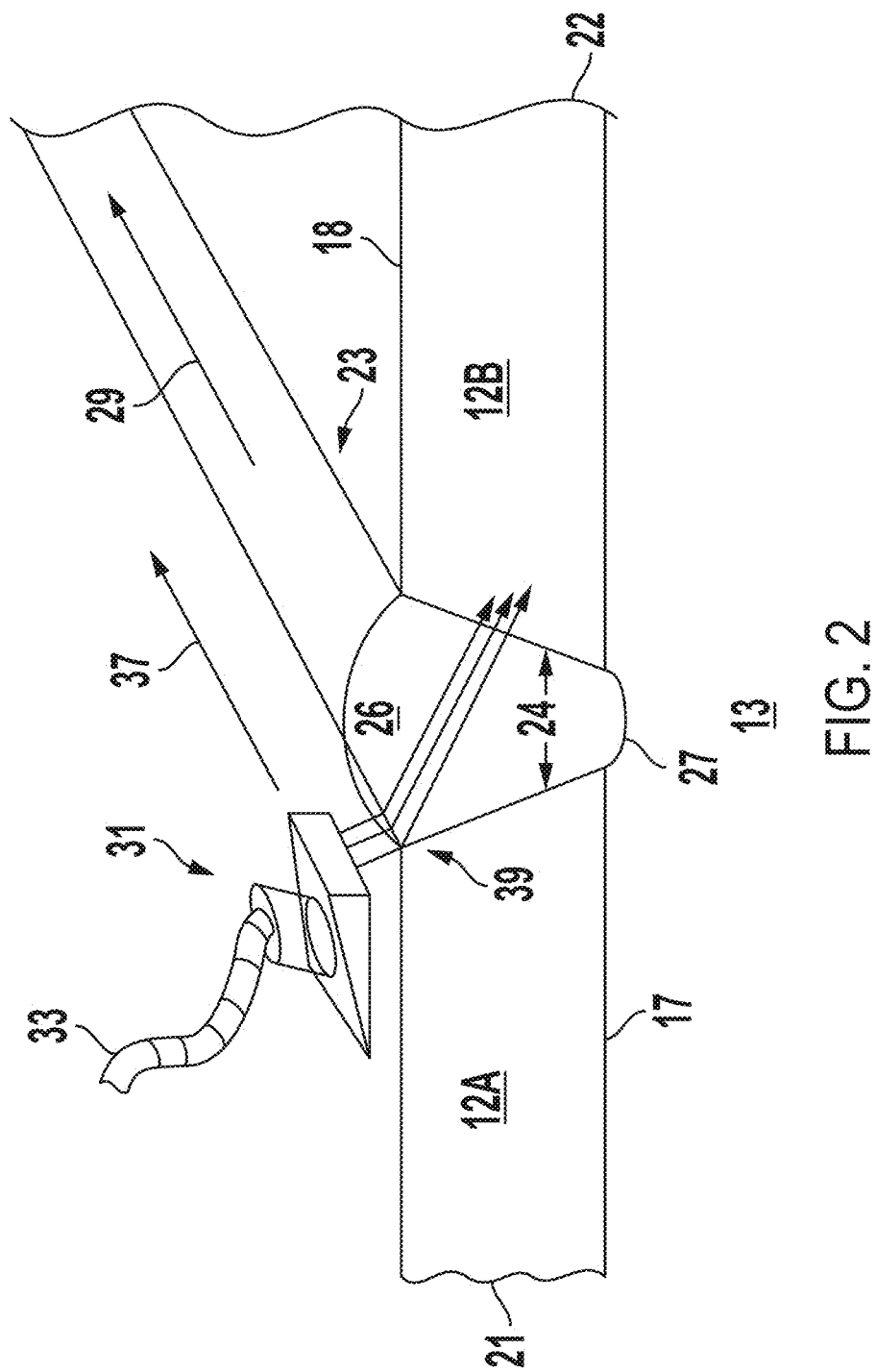
FIG. 2 is a perspective view of a typical ultrasonic testing scenario for a pipe weld seam using a phased array system or time-of-flight inspection system.

Referring to FIG. 2 probe head 31 is positioned adjacent to weld seam 23 and scanned along the length of the weld seam direction 29 joining two sections 12a, 12b of pipe 11. Since weld seam 23 has approximately a V-shape as shown in FIG. 1, the extension of seam 23 along 29 creates a wedge shaped weld seam. Testing probe 31 positioned adjacent to weld seam 23 is moved in direction 37 along the length of seam 29 while transmitting ultrasonic sound waves to the interior of the seam weld and surrounding weld metal. At all times, probe 31 tracks its position along seam 23 and its index position from the centerline of the weld seam as it scans along the weld seam. The weld seam may be scanned manually, semi-automatically, or automatically through encoded or motorized means, as is understood in the art. While the probe 31 is shown to be positioned on one side of weld seam 23, the probe may be positioned on the other side with equally effective results. In addition, multiple probes may be utilized at the same time.

Figure 3:
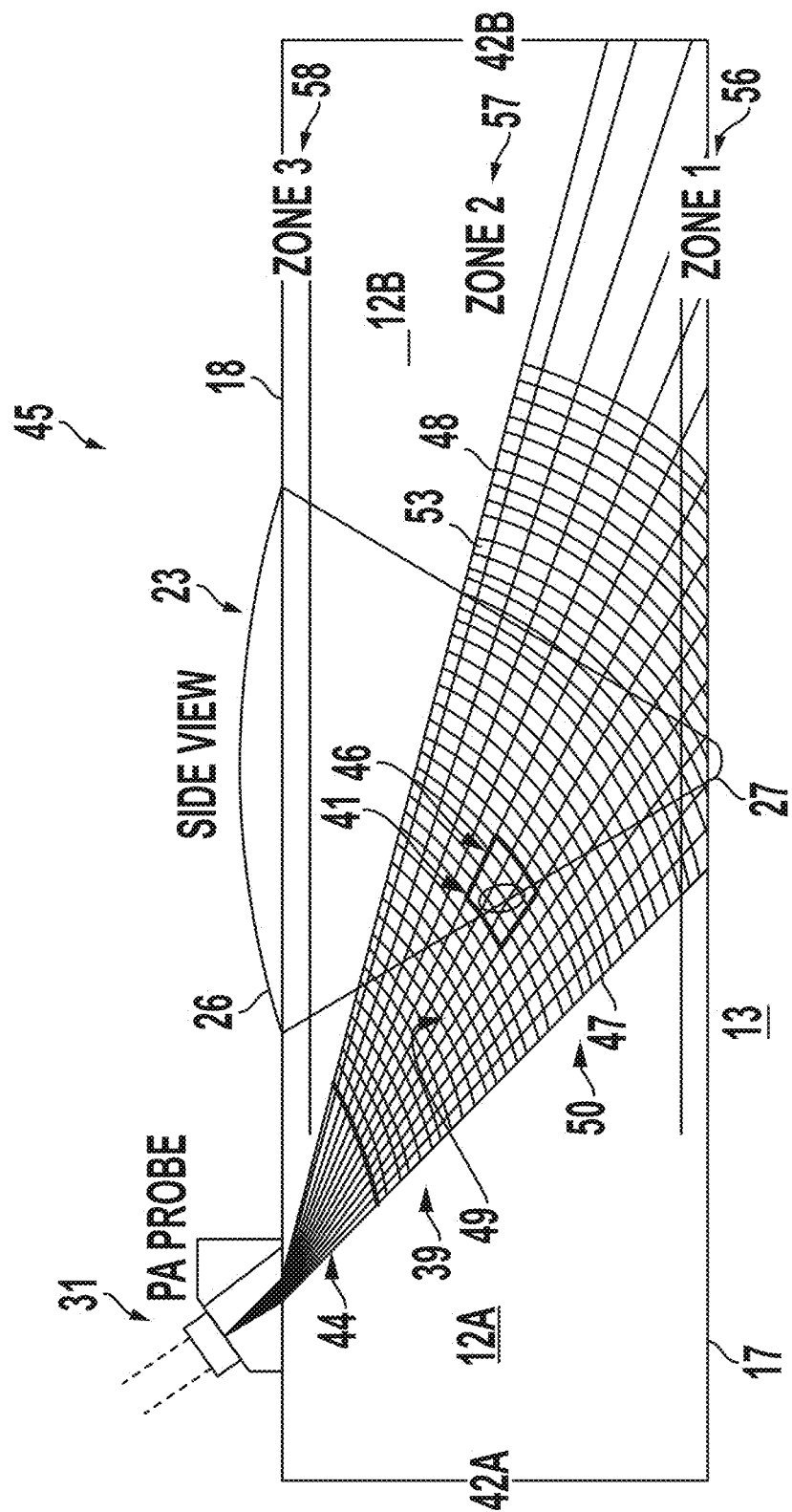
FIG. 3 is an S-scan view showing a two dimensional scan matrix overlay of refracted sound wave angles in a typical ultrasonic testing scenario for a pipe weld seam showing a potential weld flaw.

Referring now to FIG. 3 an ultrasonic data sampling system 45 of wave segments and samples is shown in a sectorial diagram similar to FIG. 1. The system 45 shows a typical sampling arrangement used in recording data from phased array or time-of-flight diffraction UT scanning of a weld seam. The diagram 45 approximates an example of a sectorial or "S-scan" view of a weld, non-destructively tested with ultrasonic waves as may be understood. Weld 23 is positioned in the middle of the system 45 having sound beam segments 39 with probe head 31 positioned at the origin of the sampling system 45. Due to the proximity to the probe, area 44 just under the probe 31 is either not included during scanning or excluded later during processing. The arrangement of the sound beam segments and sampling data points produces a two dimensional scan matrix 50 of each scan slice of data taken along weld seam 23. Each matrix 50 is not rectangular, but has a radial shape as shown, with each data point having a coordinate location of (a) scan offset, (b) beam, and (c) sample index, as will be further discussed. Hence, each data point sample 53 is composed of its three dimensional coordinate and an amplitude value representing the strength of the reflection from beams 39 at that point in space. That information can also be organized in a three dimension rectangular array in the form of a "cuboid" or a "voxel" as will be discussed in FIG. 4A.

As ultrasonic waves 39 are transmitted into the weld area 23 from probe 31 any potential weld defects 41 will produce ultrasonic reflections back to probe 31 which are received and recorded as a group of data points having elevated amplitude values. Sound beam segment 47 is approximately 45 degrees from normal, and beam segment 48 is approximately 70 degrees from normal incidence. Other angles of sound waves 39 span the angular distance between segments 47 and 48 such that the entire weld area for any current segment is covered by these scanning segments, including wave segments 49 that impinge upon potential flaw 41. Since the entire area has angles of sound waves transmitted through the base material and weld seam, any potential flaws 41 in the weld seam 23 will be contacted by one or more of the sound waves. Within the system 45, potential flaw 41 is within a bounded area 46 of data points that surrounds the potential flaw. As may be understood, the cells shown in FIG. 3 are not to scale and provided for illustrative purposes only to show the workings of the herein disclosed invention. The resolution of a typically overlay would normally be many times finer than that shown by the matrix 50.

System 45 also includes three zones of interest in any scan. Zone 1 56 is positioned along the interior surface 17 of the weld 23 and includes all data cells along that surface. Zone 3 58 is positioned along the exterior surface 18 of weld 11 and includes all data sample cells along that surface. Reflections from zones 1 and 3 may be filtered for more in-depth data analysis, depending upon the content of that data and the type of filter being applied. Zone 2 57 is positioned between zones 1 and 3 and includes all data cells not in zones 1 and 3 and are part of an analyzed set of data points in later processing.

Figure 4:
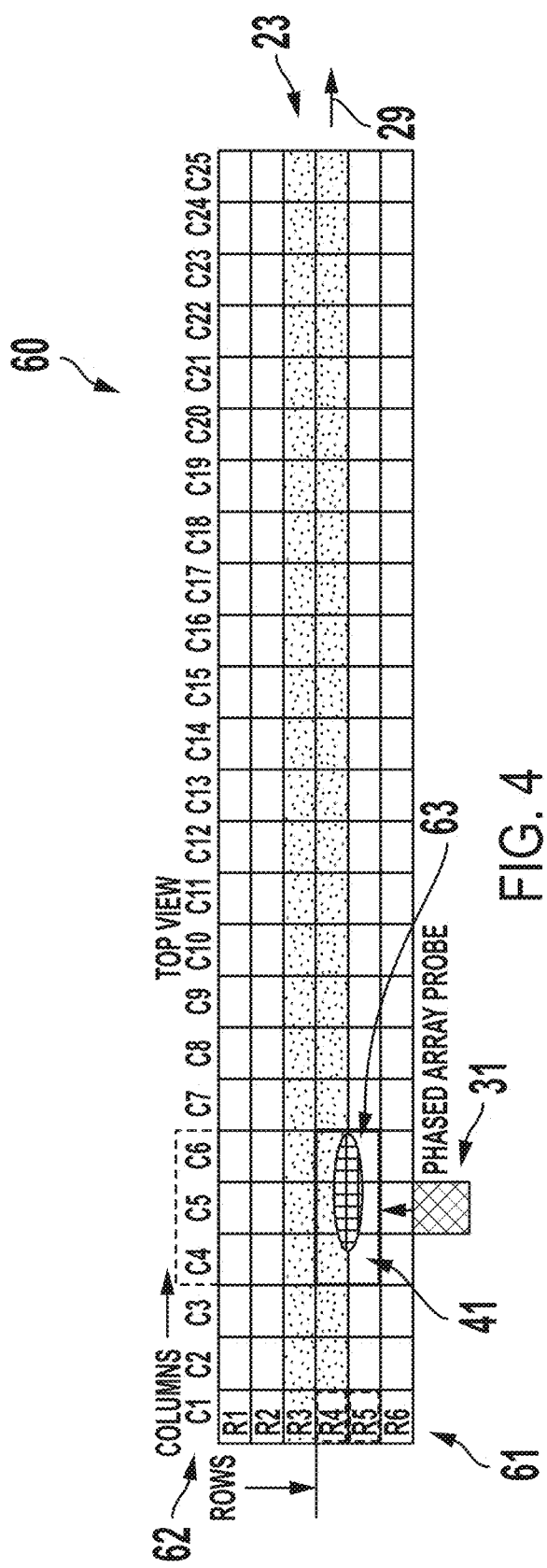
FIG. 4 depicts a plan view with a matrix overlay showing the locations and recordations of ultrasonic data on the information displayed in the graph of FIG. 3.

FIG. 4 shows a rectangular coordinate system overlaid on a top-down or "C-scan" view of the seam shown in FIG. 2. As indicated above, the coordinate system 50 is not rectangular, however because each data point has a point in three dimensional space in the scanned workpiece a corresponding point in space may be recorded in a coordinate matrix overlay 60 of data cells. In particular, the combination of rows 61 and columns 62 produces a rectangular matrix of cells that will contain each data point sample 53 in the coordinate system 60 as the probe 31 is moved along weld seam 23 (rows R3 and R4) in direction 29. Potential weld flaw 41 would be recorded in at least 6 cells, such as 63 in this depiction (i.e. R4, C4-R4, C6; R5, C4-R5, C6). A similar end-view or "B-scan" view looking into the weld having from one end with a coordinate overlay might similarly be produced and is shown in FIG. 4B. In particular, the combination of rows 161 and columns 162 produces a coordinate matrix overlay 160 of data cells viewed from the end of the weld seam 23 in either direction along 29 at a particular scan offset. Potential weld flaw 163 would be recorded in at least 6 cells 166 shown surrounding potential flaw 163. Each cell has a two dimensional measurement as depicted in FIG. 4A.

Figure 4A:
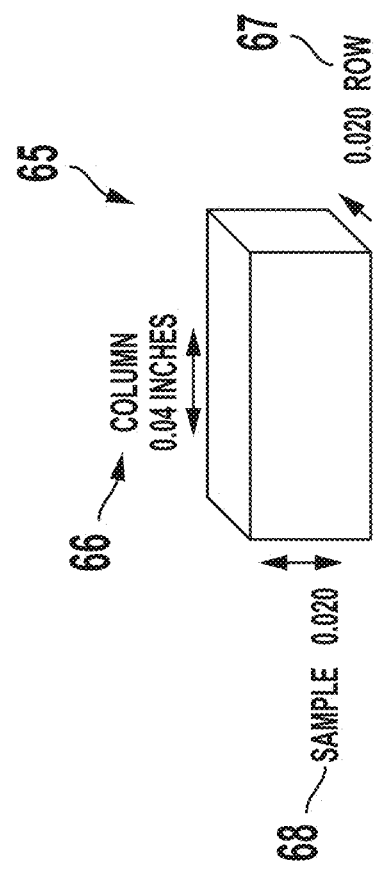
FIG. 4A is a diagram of a data cuboid.
Figure 4B:
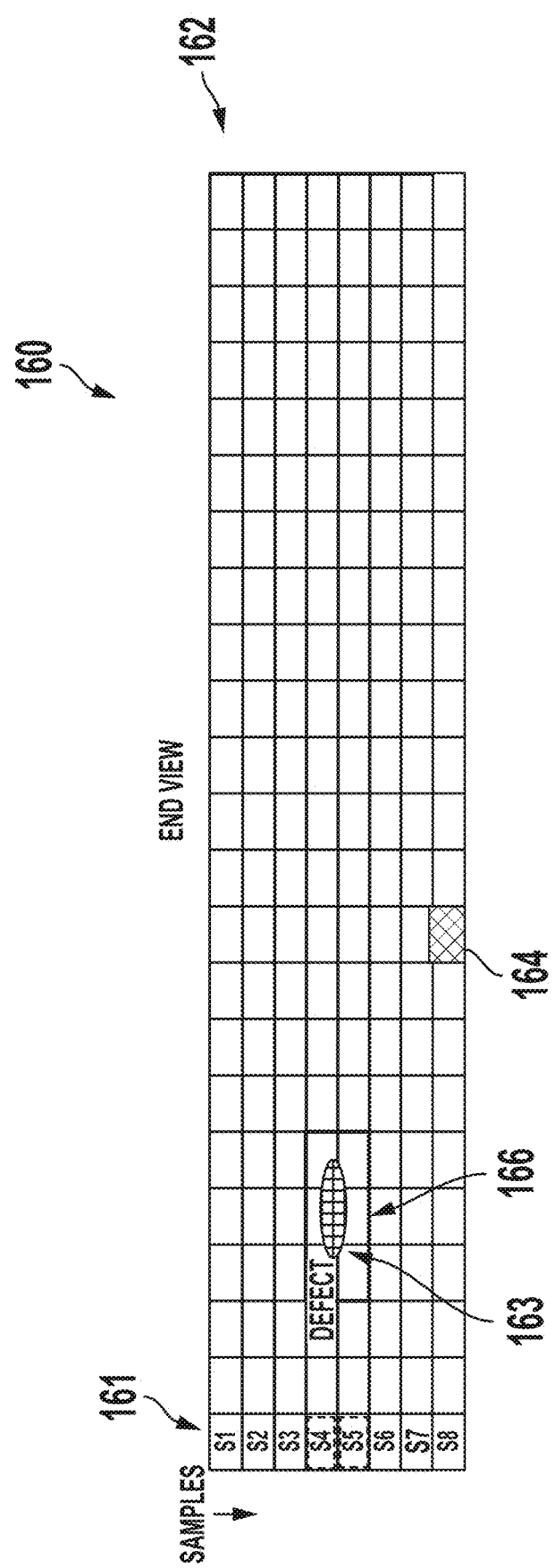
FIG. 4B depicts an end view of a weld with a matrix overlay showing the locations and recordations of ultrasonic data from the information displayed in the graph of FIG. 3.

As shown in FIG. 4A, an example of each data cell referred to hereinafter as a "cuboid" (or "voxel") or "data cuboid" 65 has length 66 of about 0.04 inches, a width 67 of about 0.02 inches, and height 68 of about 0.02 inches. As will be understood, these values may change based upon a variety of factors associated with each weld scan. While the coordinate systems shown in FIGS. 3 and 4 are two dimensional, in reality each scan snapshot taken along seam 23 has a sample width of 0.02 inches due to the way in which ultrasonic waves are transmitted into the material. Hence, each cuboid 65 is in reality three dimensional. UT probe 31 takes sectional scan snap-shots along weld seam 23 along travel path 37 (see FIG. 2) with each section scan recorded as a matrix of cuboid data values in a file, adding a new matrix section of data with each new sectional snap-shot.

Each recorded data cuboid has a set of values associated with it, comprising the prior noted three dimensional coordinate set of system 45 (see FIG. 3) and an amplitude value. The coordinate portion includes the values of depth from the top surface of the pipe also referred to as (1) the "ultrasonic axis" distance; (2) an index axis (or "index offset") which is the distance from the center line of the weld 23; and (3) a "scan axis" value (or "scan offset") which is the distance along the weld as recorded by the probe as it travels along path 37. The amplitude value is a reflection value (i.e. a sound intensity value) recorded by the probe 31 normalized to a relative value of between 0% and 100%.

In actuality, each scan section includes raw data position values of (1) scan position of the probe head as it tracks along the weld seam, (2) an angle value representing the angle of a wave segment as it is emitted from the probe emitter, typically between 45 and 70 degrees, and (3) a sample index value which is the distance from the probe emitter. Using a known set of geometric calculations for polar coordinates, any scan data value position in any data cuboid may be determined when data values are retrieved from the scan data file ("SDF") as will be discussed.

Figure 5:
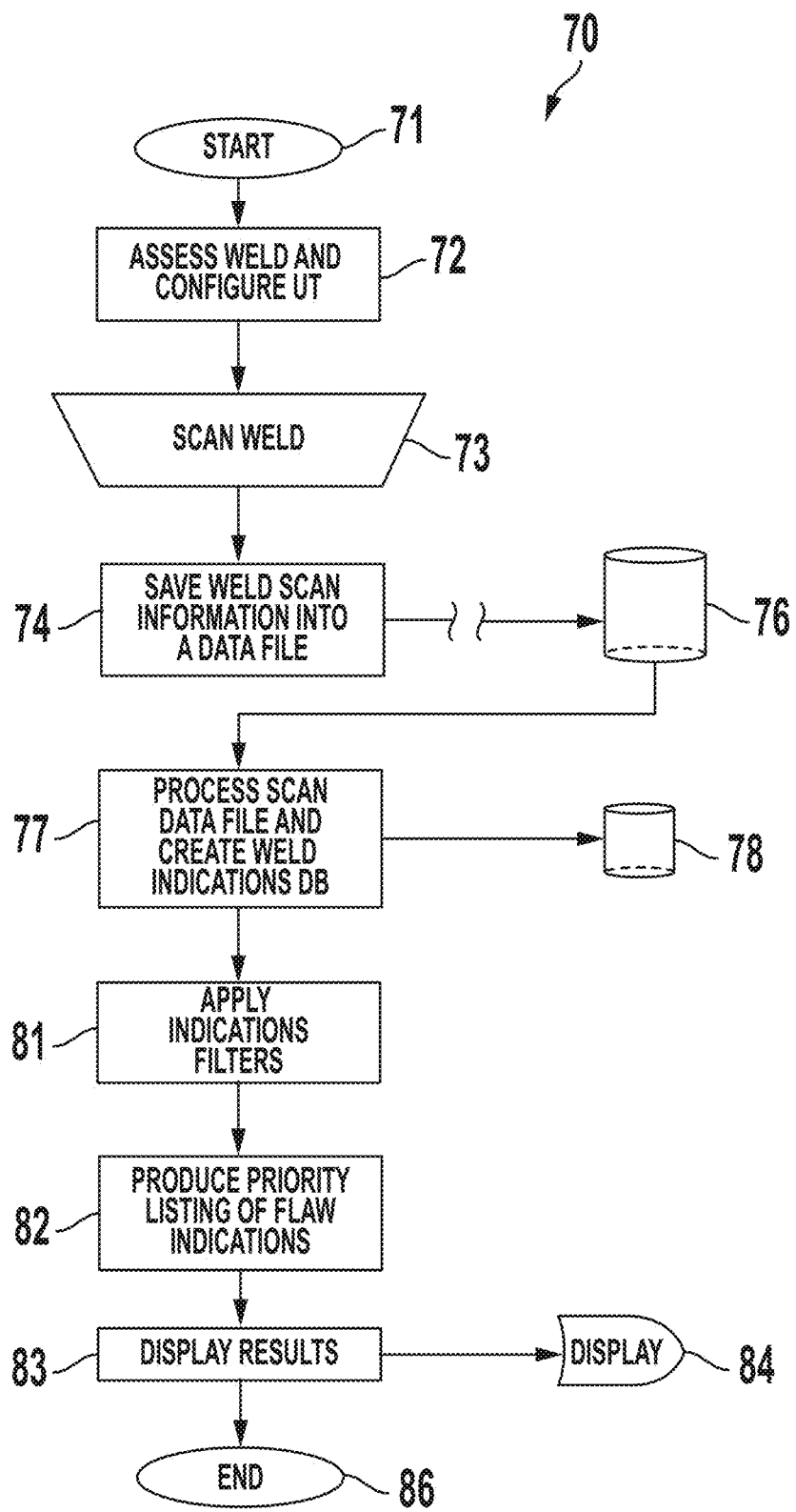
FIG. 5 is a process flow diagram of the overall invention process.

Referring now to FIG. 5 a system is presented 70 that reduces the number of weld scan indications that an inspector must review in order to produce a report meeting applicable welding examination codes and requirements, such as those published by ASME, AWS, or other organizations. The system 70 is a standard software application that may run on a standard Windows™ operating system, such as for example Windows 7 sold by Microsoft Corporation, running on a standard PC configuration. The system may also be incorporated as a module directly into existing testing and/or scan analysis software. Initially, an inspector assesses a weld situation and then configures their UT equipment for a scan, including the positioning of the UT probe 72 adjacent to a target weld. The weld is scanned by the inspector 73 and a data file recording the weld scan data saved 74. The data may be saved locally on the UT device, transferred to a connected drive storage 76, or uploaded to a network drive via Wi-Fi or other data connection, depending upon the size of the data file. The scan file is then processed 77 by extracting all data cuboids that include potential weld flaw indications, essentially extracting all cuboids that have amplitudes greater than 0, and then creates a file recording those indications and saves it in a local, fast access storage location 78. Further processing occurs on the indications file by applying a series of filters 81 that ranks and categorizes the indications into a usable form. In particular, a ranked list of indications is created in a table based on a ranking value for each indication which consists of multiple data cuboids. That priority listing of indications is then produced 82 and displayed 83 for the inspector's analysis at a place and time of their choosing. The process shown in 70, typically removes over 95 percent of the non-relevant data stored in a scan data file, and presents a focused list of only a fraction of the overall indications held by a scan data file, without degrading an inspector's ability to properly review the scan data in accordance with applicable code requirements.

Figure 6:
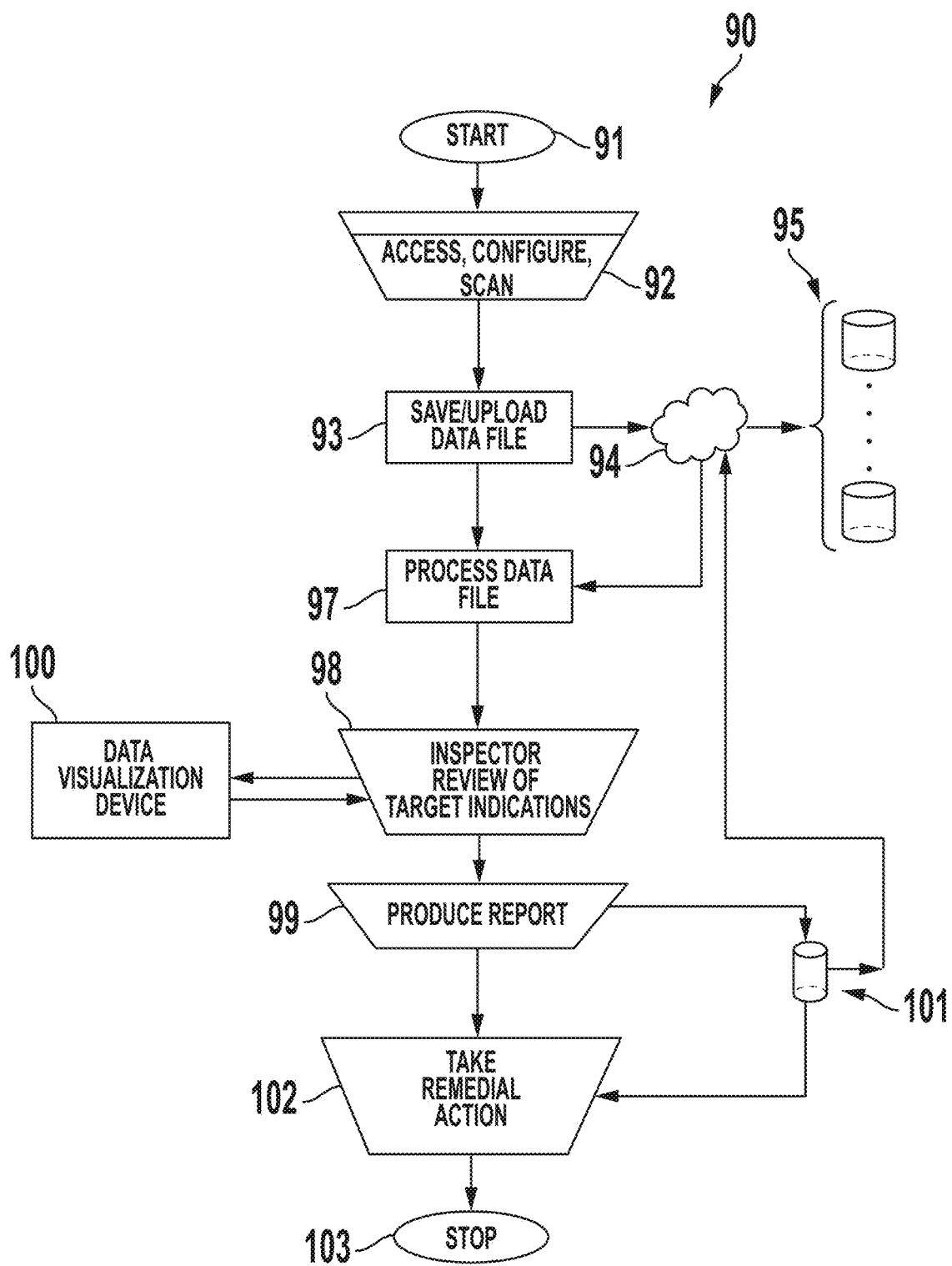
FIG. 6 is another process flow diagram of the invention process.

FIG. 6 shows the benefit of this system 70 in a typical operation 90 by an inspector. A phased array UT is arranged, configured, and then used to scan a weld under review 92. A scan data file is created and that file is saved locally, or at a remote storage location such as a cloud based drive 95 via the internet 94. The data file is then accessed at a later time and processed 97 to extract its weld indications and filtered to remove indications that do not merit review. That processing 97 may occur at the initiation of an inspector, or it may be automated upon the arrival of the data file at storage location 95. The inspector will review the published report of target indications 98 and using a compatible scan data visualization application or device 100 review each indication listed in the published indications report that merits careful study. The inspector may then produce their own inspection report 99, saving it in a local storage location, and may take remedial action 102 to correct any noted weld defects.

Figure 7:
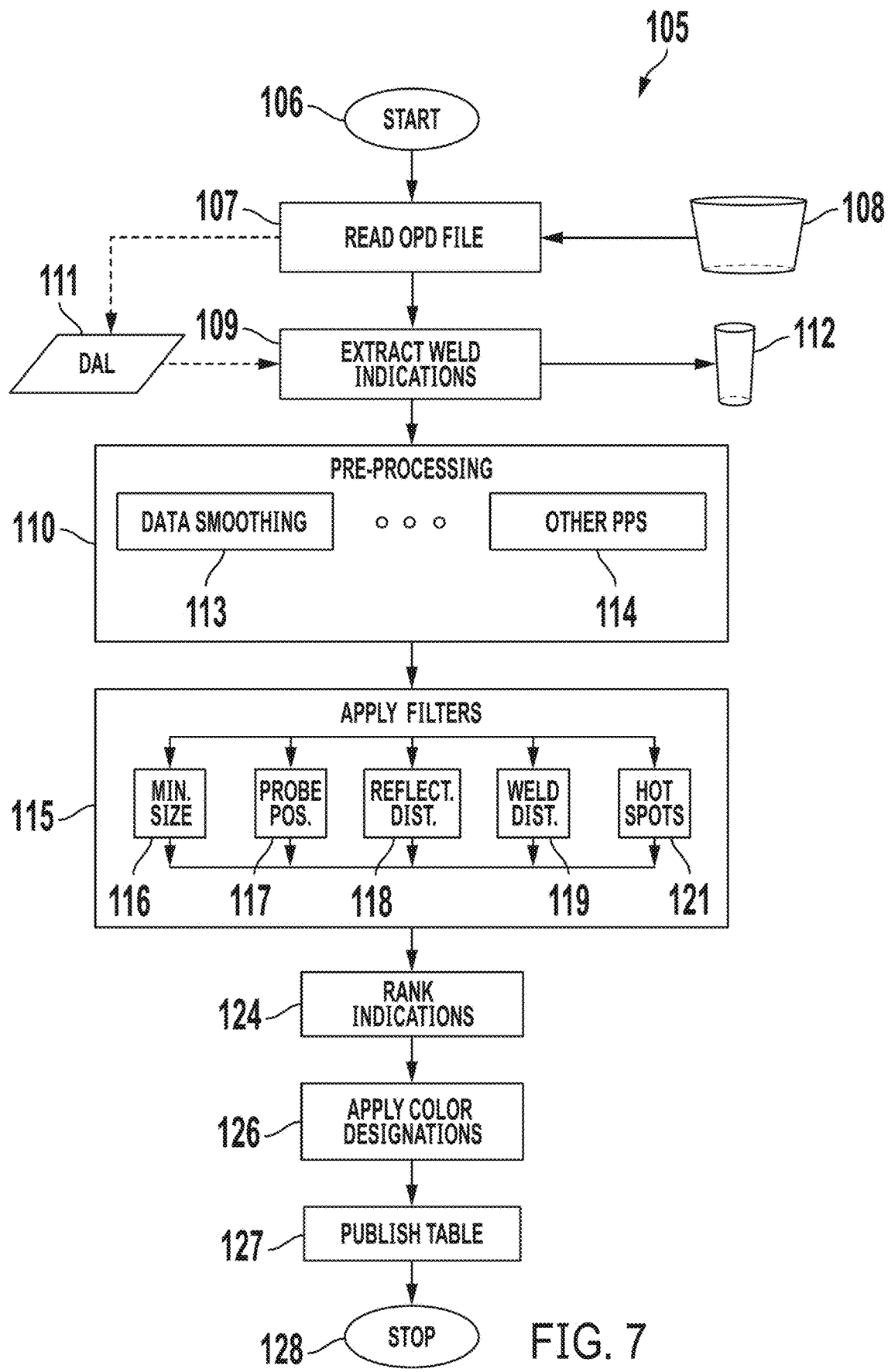
FIG. 7 is a process flow diagram showing the data filtration process utilized in the invention; and, FIG. 8 is a representative depiction of a spreadsheet chart produced by the invention after processing of weld indications showing color coding.
Figure 8:
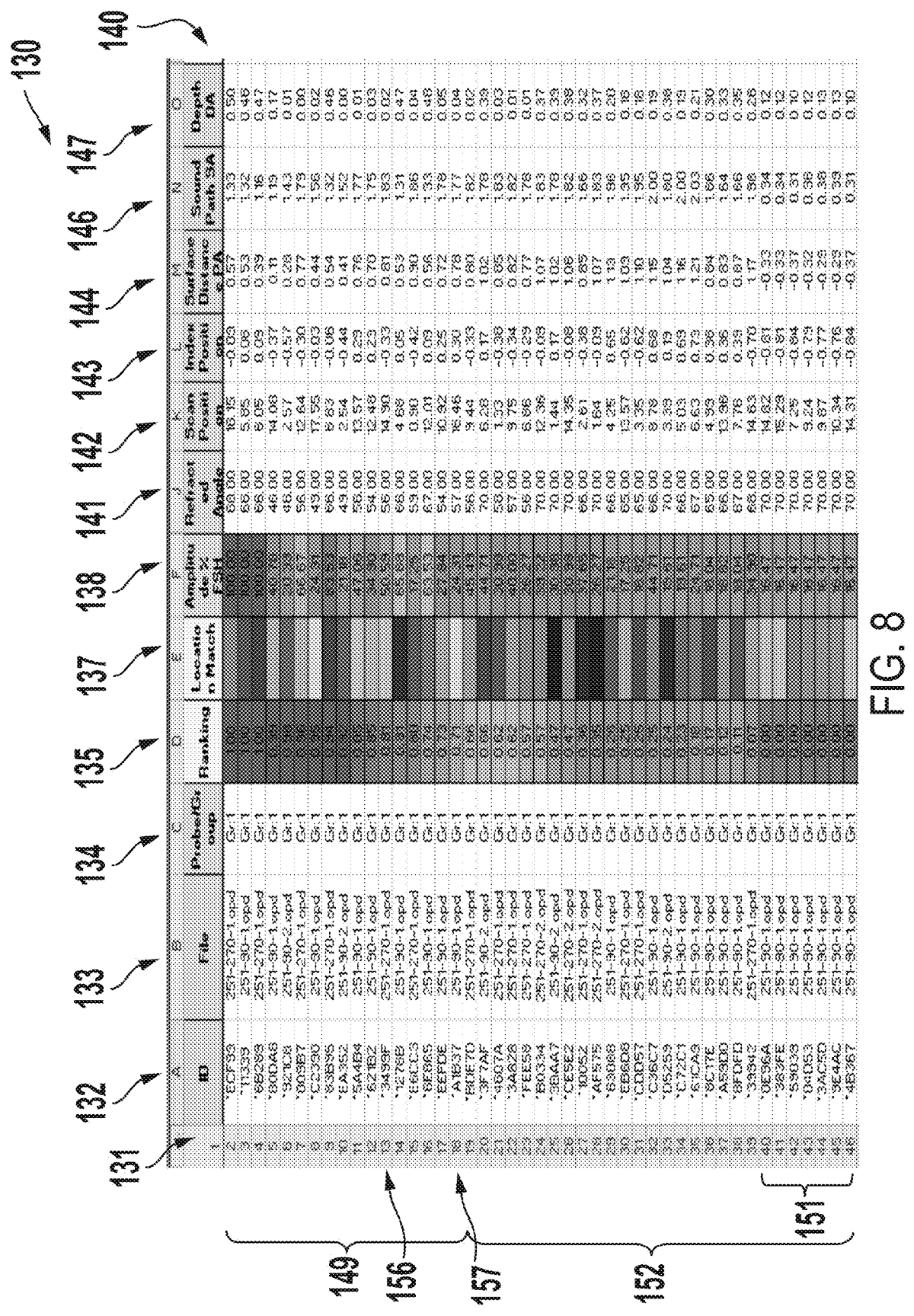

Turning now to FIGS. 7 and 8, it may be seen the detailed operation of the system 70 along with an example report table produced by the system in a typical pipe weld seam situation. A typical industry UT device is an Olympus OmniScan™ MX2 phased array flaw detector. That device produces a scan data file in the form of an OmniScan Phased Array Data File or "OPD" file. The OPD file may be saved in a storage location for later review and accessed by various visualization applications to graphically review any portion of the scan along a pipe weld seam. Each OPD file includes configuration and setup information such as weld type, weld bevel angle, thickness of the pipe material, the ultrasonic velocity utilized, probe scan and index offset, and probe skew, and also includes information on how many scan jobs are included in the file. Additionally the overall scan length is recorded and a sound path minimum value recorded. That information is utilized by the process 105 as will be discussed.

As shown in the process 105 of FIG. 7 an OPD file is read 107 from a storage location 108. The accessing of data in the OPD file may be accomplished with the help of an intervening software module known as a data access library or "DAL." The DAL is typically written or authorized to be written by the author of the OPD file specification, which in this example is Olympus NDT. Whether read directly from the OPD file, or indirectly through the use of a DAL, the data is retrieved in the form of a scan position, a beam number (i.e. beam angle), a sample index (i.e. sample number along the beam), and a data point value (i.e. magnitude) at the corresponding sample. System 105 accesses the OPD file by making a data retrieval request pursuant to an instruction format specified by DAL 111 which allows the extraction of all data cuboids in the scan data file. Any data scan cuboids accessed but having no amplitude are not saved, so only cuboids that are potentially part of a weld indication are retained. A local database file is created to hold those indications in a three dimensional matrix referenced by position and amplitude values, which is then stored 112.

The system further examines the amplitude of each data cuboid in the database and excludes any cuboids that have a value less than or equal to 16%. Sixteen percent is a value derived from weld code specifications below which scan reflection data does not typically need to be reviewed by an inspector. Each data cuboid remaining in the database is then analyzed to determine if any adjacently positioned cuboids to the one being analyzed also have been retained (i.e. their intensity values were also above 16%, see e.g. FIG. 3, 46, FIG. 4, 63). A first cuboid is considered adjacent to a second cuboid if they differ by only one position in scan, beam, and/or sample coordinate(s). Such remaining contiguous cuboids are then grouped together and referred to as an individual "indication" to signify a potential flaw indication that requires an inspector's review. Each cuboid is similarly analyzed until each cuboid is assigned into a unique weld indication 109. Several properties of each weld indication are also calculated and utilized in further processing of each indication. Namely, information such as depth, index position, and scan position range limits are recorded; the maximum intensity position within the indication is calculated to give a sense of a "center of gravity" for each indication; and the maximum amplitude of all cuboids in the indication is recorded 112.

Each indication is also given a unique ID based on a hashing of cuboid data contained in the indication. As may be understood, any identical A-scan data will always produce the same unique hash ID for each indication. Further, the process 105 also assigns a significance score to each indication to produce a priority ranking order of indications needing attention 124 as will be discussed. That significance score is a value assigned to each indication between 0 and 1, with 1 being the highest value, and represents a best estimation on the part of the process 105 to draw the attention of the inspector to an indication that is more likely to be a flaw.

Once the weld indications have been extracted 109 and saved 112, the saved data file may be pre-processed 110 to optimize the data file for filter application. For example, a data smoothing processing algorithm may be applied to the data 113 to increase the signal to noise ratio to facilitate the recognition of meaningful indications. Other preprocessing steps may be performed for different data enhancement results 114 prior to filtering the data.

A series of filters 115 are applied to each indication that affects the significance score and which is used to form a ranking 124 of each unique ID. Each flaw indication is ranked in a table based on this significance value as will be discussed in FIG. 8. Each indication starts with an initial value of 1, and resulting filter values are multiplied together and then multiplied by 1. Hence, and as will be seen, some filters are essentially fully exclusionary because they only return either a 1 or a zero. Other filters return a value between 0 and 1 that may reduce the significance score of the indication or leave it at 1.

Filter 116 is a minimum size filter 116 which is applied to each indication. If an indication is below a minimum threshold size, that indication is assigned a significance score of zero. Specifically, if an indication includes a number of contiguous cuboids less than a threshold value, a zero is assigned to that unique indication ID. Alternatively, a 1 is returned if the filter 116 does not apply. Currently, the ASME code specifies threshold values of 0.08 inches length (scan dimension), 0.06 inches width (index dimension), and 0.06 inches height which might change with each particular scan situation.

Also, any flaw indications that are too close to the probe emitter 117 (see FIG. 3, 44) returns a value of zero which would result in a significance value of zero. Indications are discarded (i.e. assigned a zero score) due to the distortions that are experienced near the probe head in the pipe material. So, any indications that are within 25% of the scanned workpiece thickness from the probe head are assigned a zero significance score 117. Alternatively, a 1 is returned if the filter 117 does not apply.

Reflection of sound waves is timed in each UT device and any indications that are more distant than a predetermined percentage of the pipe steel thickness distance (e.g. indications in Zones 1 and 3 of FIG. 3), and also as set by welding code specifications, are assigned a zero significance score 118. Alternatively, a 1 is returned if the filter 118 does not apply.

Also, any reflections that are more distant than a set lateral distance from the weld 23 are assigned a value 119 between zero and 1 representing a reduction in significance in that indication the farther away an indication is it positioned away from the weld centerline. The significance factoring for filter 119 is shown in the processing pseudo code of Table 1 below.

TABLE 1

Let MAX = maximum distance from weld before an indication may be disregarded by the code (currently this value is 2" if the part thickness is 8" or more, otherwise the minimum of 1" or the part thickness).

TABLE 1-continued

If an indication is farther away than MAX from the weld it is considered not in the "heat affected zone" or HAZ.
Let DIST = the lateral distance (i.e., in the index offset dimension) of the indication from the weld surface.
Let D1 = DIST/MAX
If D1<= 0.25, return score = 1.0
If D1 >= 1.0 return score = 0.0.
Otherwise return score = (D1 − 0.25)/0.75
(i.e. linearly interpolate).

As part of the UT scanning process, it is typical that some inherent noise echoes or "hot spots," also known as "root or weld cap geometry signals," will be created for each sectorial scan as the probe traverses along the weld seam. Essentially, these false returns are artifacts that are produced by the geometries of the top and bottom weld caps. The nature of these hot spots is that they are periodically repeated along the seam at regular intervals and typically have common characteristics between one another, namely they appear at substantially the same index offset and depth locations. Since these hot spots represent false flaw indications, filter 121 assigns a reduction in significance score to all such indications which are likely to be false returns due to these ultrasonic geometries. The significance factoring sub-process for filter 121 is shown in the processing pseudo code of Table 2 below.

TABLE 2

Let S = {s1, b1, m1}, {s2, b2, m2}, . . . , be the set of 3D coordinates (in Scan, Beam, and saMple) of all voxels/data points within the indication. This will represent a contiguous region/blob of data points in 3 dimensions. Each data point will have an associated amplitude measured from 0 to 100.
Let MAX = maximum amplitude of all of the amplitudes of all the coordinates in S.
Let P = {b1, m1}, {b2, m2}, . . . be the set of 2D coordinates in beam and sample dimensions that results when you take all of the 3D coordinates in S and simply discard their scan coordinate; if there are any duplicates, discard the duplicates.
(i.e. P is the projection of S along the scan dimension).
For each coordinate {b', m'} in P, let TYPICAL(b', m') be the average amplitude over all data points {s', b', m'}, where s' ranges over all possible values except for those values where {s', b', m'} is a member of S.
For each {b', m'} in P, let RATIO(b', m') = MAX/TYPICAL (b', m').
Let AVGRATIO = average of RATIO(b', m') over all points {b', m'} in set P.
If AVGRATIO >= 2.0 then return score 1.0
If AVGRATIO <= 0.25 then return score 0.0
Otherwise, return score = AVGRATIO − 0.25)/1.75
(i.e. linearly interpolate).

As may be understood, the filters incorporated in 115 may be altered in their variables and operation to lesson or increase their individual effects on an indication's significance score. In addition, more filters might be incorporated in the future as weld specifications and codes are updated, or resulting from better understanding of flaw indications present in an ultrasonic weld scan.

After filters 115 are applied to the indications held in database 112, the indications are ranked 124 based upon their resultant significance values. Color designations are then optionally applied 126 to each ranked indication to assist an inspector in correlating the same instance of an indication over multiple scanning data files. A designation ranking table is then published 127 for the inspector's use in evaluating an OPD data file.

FIG. 8 shows an abridged ranking report of flaw indications that can be relied upon by an inspector to focus their attention on important indications. The chart 130 is used for example purposes only and as will be understood any real weld scan data file would likely include hundreds of indications, but chart 130 is abridged to show only 45 entries for illustration purposes but still show the usefulness of the report. The chart 130 is a spread sheet and displays 45 rows each representing a flaw indication ranked in order of significance from 2 to 45 in rows, row 2 being the most important flaw indication and row 46 the least significant indication. Each indication is assigned a unique ID created via a hashing function as shown in column A 132. Also, a series of columns with headings 140 provides characteristic information on each indication. Individual entries in column A 132 may be hyperlinked to views in a cooperative data scan visualization program allowing for direct selection of any indication in the chart for instant viewing in the scan visualization application. Column B 133 displays the scan file from which the indication was produced, and as can be seen at least 4 different scan files were processed by system 105 to produce the table 130. The chart also indicates the probe group from which the samples were taken 134. Rankings shown in Column D 135 list all indications retrieved from the scan data file in descending order from the highest value of 1.00 to the lowest value of 0.00. Alternatively, the chart may be reordered to arrange indications in a direction running along the weld length. Column F 138 shows the maximum amplitude of any cuboid present in any indication, typically close to the center of gravity of any indication. The refracted angle of the indication is shown in Column J 141. The scan position, index position, and surface distance are shown in columns K 142-M 144. The sound path is shown in column N 146, and the indication depth is shown in column O 147.

Color coding is also optionally utilized to assist an inspector in recognizing certain attributes of indications. First, rankings in column D 135 are assigned a graduated scale from red to blue using the color spectrum to show a high ranking to a lower ranking. For example, the top 10 entries in rows 2-11 have a bright red color indicating importance, importance. Location match column E 137 displays a color based on location for each indication by assigning color values from a color palette to the center of gravity value of each indication and using depth of the center of gravity indication as a red value, using the scan position of the center of gravity indication as a green value, and using the index position of the center of gravity indication as a blue value. Hence, even if multiple scan files are produced and analyzed in the process 105, a color location match will assist the inspector in recognizing repeated indications for the same position along the weld seam. So, for example, entries on rows 13 and 18, which come from different scan data files, are likely from the same three dimensional location along the seam because they have similar colors listed in column E 137. Finally, amplitudes are color coded to indicate their relative position between 0% and 100% similarly to the assignments of ranking. However, because high amplitudes do not necessarily lead to high ranking, colors do not show as a graduated scale in the present example, as in column D 135 for instance, because the indications ranking of 130 is sorted on ranking and not on amplitude value. Nevertheless, the color does provide a visual indication of amplitude that may be useful when correlating a particular indication in a scan visualization application to the chart 130.

As may be seen, entries 2-18 149 show rankings from 1.00 to 0.71. These rankings would likely be the most important indications for an inspector to review on the scan visualization application to determine whether remedial action is necessary. Lower entries 152 and 151 may not need to be reviewed or reviewed with less scrutiny than usual. Entries 40-46 151 probably need no or only cursory attention from the inspector. Also, as might be understood, the listed indications might be re-sorted in additional tabs under chart 130 to further assist in focusing the inspector on indications of interest. For example, a subsequent tab might list only the top 30 indications.

Overall an inspector having to review the four listed scan files in scan visualization software would take a great deal of time to review each and every indication, but using the chart shown in FIG. 8 an inspector can quickly focus their attention on indications that merit detailed scrutiny.

While I have shown my invention in one form, it will be obvious to those skilled in the art that it is not so limited but is susceptible of various changes and modifications without departing from the spirit thereof Having set forth the nature of the invention, what is claimed is:

1. A method for efficiently reviewing weld scan data by a weld inspector, comprising the steps of:
    a. accessing a stored ultrasonic scan data file;
    b. causing the processing of said stored ultrasonic scan data file to extract a set of weld indications;
    c. causing the ranking of said set of weld indications from most likely to be a flaw to least likely to be a flaw;
    d. reviewing said set of ranked indications;
    e. accessing a scan data visualization application and reviewing a subset of said ranked indications on said visualization application; and,
    f. producing a report on said weld based on said reviewing step by said weld inspector.

2. A method as recited in claim 1, wherein said step of causing the extraction of weld indications from said scan data file comprises the steps of:
    a. extracting all cuboids held by said scan data file having a non-zero magnitude value and saving those cuboids in an indications data file along with three dimensional position information within said weld for each said cuboid; and,
    b. assigning a unique group identifier for all cuboids in said indications data file that are positioned immediately adjacent to one another in said weld such that each group identifier represents a separate weld indication.

3. A method as recited in claim 2, wherein said step of causing the extraction of weld indications from said ultrasonic scan data file further comprises the step of comparing the magnitude of each said cuboid to a predetermined value and excluding any cuboids that do not exceed said predetermined value prior to said step of assigning a unique group identifier.

4. A method as recited in claim 3, further comprising the steps of:
    a. applying a plurality of computational filters to each weld indication, wherein each said filter results in a numerical weighting factor;
    b. combining the numerical weighting factors to form a combined single weighting factor for each weld indication; and,
    c. applying said combined weighting factor to a normalized value assigned to every weld indication and forming said ranked list of weld indications based upon said weighting factor application.

5. A method as recited in claim 1, further comprising the steps of:

a. applying a plurality of computational filters to each weld indication, wherein each said filter results in a numerical weighting factor;

b. combining the numerical weighting factors to form a combined single weighting factor for each weld indication; and, c. applying said combined weighting factor to a normalized value assigned to every weld indication and forming said ranked list of weld indications based upon said weighting factor application.

6. A method as recited in claim 1, wherein said reviewing step further includes the steps of:

a. comparing a location based color coding set in said ranked indication and identifying all entries that have identical colors; and, b. identifying likely flaw indications based upon a pre-assigned color.

7. A method as recited in claim 1, wherein said step of causing the processing of said stored ultrasonic scan data file to extract a set of weld indications occurs on a computing platform remotely located from the location of a weld site represented by the stored ultrasonic scan data file.

8. A method as recited in claim 1, wherein said processing step includes preprocessing said scan data file.

9. In a pipe having a weld seam connecting at least two portions of said pipe and an inspection system at the site of the weld comprising an ultrasonic testing device, an ultrasonic probe attached to said testing device positioned adjacent to said weld seam, a ultrasonic scan data file holding data representing an ultrasonic testing scan of said weld seam created by said ultrasonic testing device, a method for efficiently reviewing weld scan data by a weld inspector comprising the steps of:

a. ultrasonic scanning the weld seam;

b. saving the ultrasonic scan data file to storage;

c. processing the ultrasonic scan data file to create a listing of weld indications ranked in order of inspection importance;

d. said weld inspector utilizing the ranked listing of indications to guide them in reviewing the ultrasonic scan data of the weld seam; and, e. said weld inspector producing a report incorporating at least a portion of said ranked listing in combination with their inspection results of the weld seam.

10. A method as recited in claim 9, wherein said step of causing the extraction of weld indications from said scan data file comprises the steps of:

a. extracting all cuboids held by said scan data file having a non-zero magnitude value and saving those cuboids in an indications data file along with three dimensional position information within said weld for each said cuboid; and, b. assigning a unique group identifier for all cuboids in said indications data file that are positioned immediately adjacent to one another in said weld such that each group identifier represents a separate weld indication.

11. A method as recited in claim 10, wherein said step of causing the extraction of weld indications from said ultrasonic scan data file further comprises the step of comparing the magnitude of each said cuboid to a predetermined value and excluding any cuboids that do not exceed said predetermined value prior to said step of assigning a unique group identifier.

12. A method as recited in claim 11, further comprising the steps of:

a. applying a plurality of computational filters to each weld indication, wherein each said filter results in a numerical weighting factor;

b. combining the numerical weighting factors to form a combined single weighting factor for each weld indication; and, c. applying said combined weighting factor to a normalized value assigned to every weld indication and forming said ranked list of weld indications based upon said weighting factor application.

13. A method as recited in claim 12, wherein said step of causing the processing of said stored ultrasonic scan data file to extract a set of weld indications occurs on a computing platform remotely located from the location of a weld site represented by the stored ultrasonic scan data file.

14. A method as recited in claim 9, wherein said reviewing step further includes the steps of:

a. comparing a location based color coding set in said ranked indication and identifying all entries that have identical colors; and, b. identifying likely flaw indications based upon a pre-assigned color.

15. A method as recited in claim 9, wherein said step of causing the processing of said stored ultrasonic scan data file to extract a set of weld indications occurs on a computing platform remotely located from the location of a weld site represented by the stored ultrasonic scan data file.

16. A method as recited in claim 9, wherein said processing step includes preprocessing said scan data file.

17. A method as recited in claim 16, wherein said processing step of said scan data file to produce a set of weld indications produces said set of weld indications in an OmniScan Phased Array Data file format and includes an internal data table of weld indications meeting a pre-selected weld indications criteria.

18. A method as recited in claim 17, wherein said weld indications in said internal data table comprises a cuboid.

19. A method as recited in claim 18, wherein said step of producing a report produces a viewable listing of said internal data table of weld indications.

20. A method as recited in claim 9, wherein said step of producing a report produces a viewable listing of an internal data table of weld indications held by said ranked listing.

* * * * *